United States Patent
Cardarelli et al.

(10) Patent No.: US 8,832,558 B2
(45) Date of Patent: Sep. 9, 2014

(54) PREDETERMINED PRESENTATION OF PATIENT DATA AT BEDSIDE

(75) Inventors: Marcelo G. Cardarelli, Lutherville, MD (US); Vinay Vaidya, Scottsdale, AZ (US); Yan Xiao, Plano, TX (US)

(73) Assignee: University of Maryland, Baltimore, Baltimore, MD (US)

( * ) Notice: Subject to any disclaimer, the term of this patent is extended or adjusted under 35 U.S.C. 154(b) by 501 days.

(21) Appl. No.: 13/120,921

(22) PCT Filed: Oct. 9, 2009

(86) PCT No.: PCT/US2009/060246
§ 371 (c)(1),
(2), (4) Date: Mar. 25, 2011

(87) PCT Pub. No.: WO2010/042872
PCT Pub. Date: Apr. 15, 2010

(65) Prior Publication Data
US 2011/0179361 A1      Jul. 21, 2011

Related U.S. Application Data

(60) Provisional application No. 61/104,758, filed on Oct. 12, 2008.

(51) Int. Cl.
*G06F 3/00* (2006.01)
*G06F 9/44* (2006.01)
*H04L 12/24* (2006.01)
*G06Q 50/24* (2012.01)

(52) U.S. Cl.
CPC *G06F 8/34* (2013.01); *H04L 41/22* (2013.01); *G06Q 50/24* (2013.01)
USPC ................. 715/736; 715/771; 715/744; 705/3

(58) Field of Classification Search
CPC ........... G06F 8/34; H04L 41/22; G06Q 50/24
USPC ............................. 715/736, 771, 744; 705/3
See application file for complete search history.

(56) References Cited

U.S. PATENT DOCUMENTS 5,331,549 A * 7/1994 Crawford, Jr. ................ 600/513
5,687,717 A * 11/1997 Halpern et al. ............... 600/300

(Continued)

FOREIGN PATENT DOCUMENTS

WO        2010042872 A3      7/2010

OTHER PUBLICATIONS

European Search Report, "Examiner Analysis" pp. 1-4, Mar. 13, 2014.

*Primary Examiner* — Ryan Pitaro
(74) *Attorney, Agent, or Firm* — Evans & Molinelli PLLC; Eugene J. Molinelli

(57) ABSTRACT

Techniques for presenting patient data at the patient's bedside include receiving predetermined presentation style data that indicates a subset of fewer than all parameters available from an electronic medical records (EMR) system and a first arrangement on a display device of related parameters in the subset. Without human intervention, the most recent values from the EMR system are received. The most recent values are associated in the EMR system with the particular patient for corresponding parameters of the subset. A first most recent value is presented according to the first arrangement at the particular bedside display device without human intervention. In some embodiments, the most recent values are also received or presented in response to a single stroke from a human user at an input for the particular display device.

28 Claims, 7 Drawing Sheets

(56) References Cited

U.S. PATENT DOCUMENTS

| | | | |
|---|---|---|---|
| 5,867,821 A * | 2/1999 | Ballantyne et al. | 705/2 |
| 6,239,796 B1 * | 5/2001 | Alexander | 715/809 |
| 7,895,527 B2 * | 2/2011 | Zaleski et al. | 715/804 |
| 8,273,018 B1 * | 9/2012 | Fackler et al. | 600/300 |
| 8,291,337 B2 * | 10/2012 | Gannin et al. | 715/771 |
| 2002/0116226 A1 * | 8/2002 | Auer et al. | 705/3 |
| 2003/0204419 A1 * | 10/2003 | Wilkes et al. | 705/3 |
| 2004/0054261 A1 * | 3/2004 | Kamataki et al. | 600/300 |
| 2004/0122476 A1 * | 6/2004 | Wung | 607/5 |
| 2005/0125256 A1 * | 6/2005 | Schoenberg et al. | 705/2 |
| 2006/0074321 A1 * | 4/2006 | Kouchi et al. | 600/481 |
| 2006/0116639 A1 * | 6/2006 | Russell | 604/131 |
| 2006/0259329 A1 | 11/2006 | Kline | |
| 2007/0294114 A1 | 12/2007 | Urali et al. | |
| 2008/0004904 A1 * | 1/2008 | Tran | 705/2 |
| 2008/0201172 A1 | 8/2008 | McNamar | |
| 2008/0270080 A1 * | 10/2008 | Zong | 702/188 |
| 2009/0222286 A1 * | 9/2009 | Elsholz | 705/3 |
| 2010/0131883 A1 * | 5/2010 | Linthicum et al. | 715/771 |
| 2011/0009710 A1 * | 1/2011 | Kroeger et al. | 600/300 |
| 2011/0145894 A1 * | 6/2011 | Garcia Morchon et al. | 726/4 |
| 2013/0045685 A1 * | 2/2013 | Kiani | 455/41.2 |
| 2013/0158618 A1 * | 6/2013 | Libbus et al. | 607/17 |

* cited by examiner

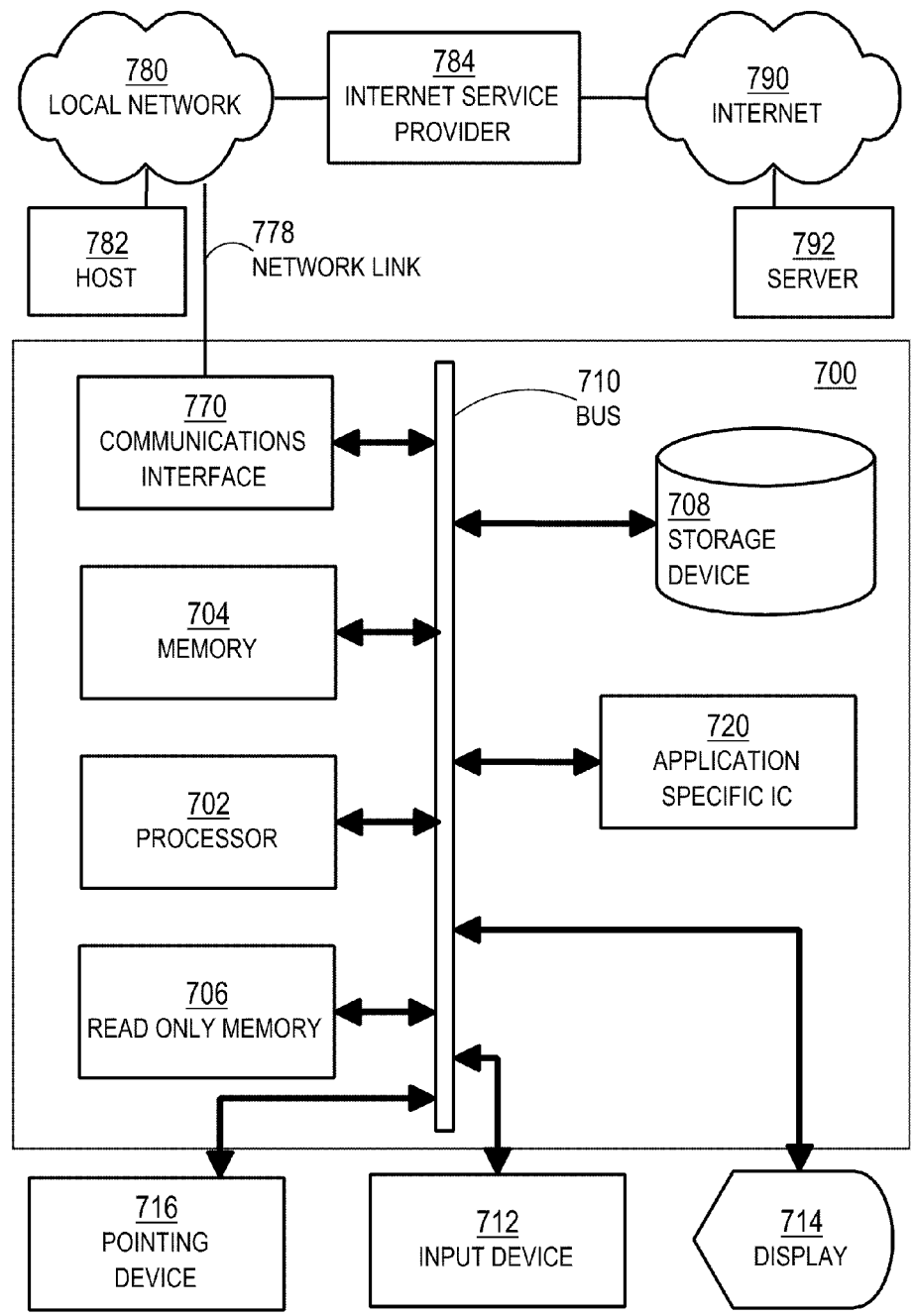

PREDETERMINED PRESENTATION OF PATIENT DATA AT BEDSIDE

STATEMENT OF GOVERNMENTAL INTEREST

This invention was made with government support under Grant Number 053646 awarded by the National Science Foundation. The government has certain rights in the invention.

CROSS-REFERENCE TO RELATED APPLICATIONS

This application claims benefit of Provisional Appln. 61/104,758, filed Oct. 12, 2009, the entire contents of which are hereby incorporated by reference as if fully set forth herein, under 35 U.S.C. §119(e).

BACKGROUND OF THE INVENTION

1. Field of the Invention

The present invention relates to patient bedside monitors.

2. Description of the Related Art

Real-time access to vital data concerning a patient, at the patient's bedside, is limited to directly measured parameters, such as an electro cardiogram (ECG) readout, oxygen saturation (O2), and blood pressures (BP). These directly measured parameters are usually called vital signs and are displayed in real-time or near real-time at the bedside on a corresponding number of viewing devices (also called monitors).

However, access to additional data vital to the immediate care of the patient (such as, but not limited to, electrolytes, gases, hemoglobin and cultures) is not immediately available at the bedside. As used herein vital data refers to all data critical to the immediate care of the patient, such as vital signs, electrolytes, gases, hemoglobin, cultures and other data, in any combination.

Electronic medical records (EMR) have been gaining acceptance in healthcare facilities. EMR systems are designed to archive all information about a patient in one or more stand alone or networked computer systems, including patient identification data, patient demographics data, patient medical history, image study reports, patient vital signs, caregiver instructions, laboratory information for laboratory orders and results, medications ordered and administered, and additional data, usually in chronologic order. EMR systems are frequently not integrated, some of which serve single purposes, such as providing laboratory information only.

To view data from the EMR systems at the bedside requires a caregiver to know or guess or spend time ascertaining what vital data are most recently available and then to request those data. Further efforts are required to arrange the data in a useful way on a presentation device, such as screen or printer.

Using conventional EMR systems is not real-time or near real-time (i.e., it is slow). It is tedious (requires the entry of many keystrokes at a computer terminal which are repetitious of keystrokes typed previously for the same patient or other patients). It is error-prone (human input is subject to typographical errors and loss of concentration due to tediousness, stress and subjective physical or mental state of the user). It is non-uniform (each request may arrange the same information in different order and screen location or arrange different information). It is not suited for more than a single viewer at one time. It requires training to identify and request data; and often requires registration and login. It moves the user from the bedside, where the patient can be viewed, to a computer terminal input device, albeit sometimes nearby.

Because of such problems, clinicians often resort to relying on dedicated personnel to provide the data needed for the daily decision making cycle. The data is often provided on paper (either printouts or manually transcribed data items read from a computer presentation device) and read aloud to a group of caregivers at the bedside. This introduces other opportunities for errors, such as errors during transcription, errors during reading (e.g., due to dyslexia or mispronunciation) and errors of aural processing by the listeners (due to distraction, hearing impairments and room noise). Furthermore, this approach consumes the time of trained personnel, a scarce resource also needed to perform other important or critical duties, such as administering medications and tending to patient comfort.

SUMMARY OF THE INVENTION

Techniques are provided for presenting patient data at the patient's bedside that do not suffer all the disadvantages of prior art approaches.

In a first set of embodiments, a method includes receiving predetermined presentation style data at a particular display device located bedside for a particular patient. The presentation style data indicates a subset of fewer than all parameters available from an electronic medical records (EMR) system. The presentation style data also indicates a first arrangement on a display device of related parameters in the subset. Without human intervention, most recent values from the EMR system are received at the particular display device. The most recent values are associated in the EMR system with the particular patient for corresponding parameters of the subset. At least a first most recent value is presented at the particular display device according to the first arrangement without human intervention.

In some embodiments of the first set, the subset of fewer than all parameters available from the EMR system excludes such parameters that are not immediately critical for determining status of or treatment for the patient.

In some embodiments of the first set, the first arrangement includes a font size on the display device for a parameter of the subset, such that a value of the parameter is visible on the display device to multiple viewers more than five feet from the display device. At least the first most recent value is presented according to the font size.

In some embodiments of the first set, the first arrangement includes multiple colors to distinguish a normal and stable value from a value trending toward an abnormal range or in a dangerous range. At least the first most recent value is presented in one color to indicate whether the first most recent value is a normal and stable value or a value trending toward an abnormal range or in a dangerous range.

In some embodiments of the first set, the most recent values also are received or presented, or both, in response to a single stroke from a human user at an input for the particular display device.

In a second set of embodiments, a method includes sending most recent values from an electronic medical records (EMR) system without human intervention to a particular display device located bedside for a particular patient. The most recent values are associated in the EMR system with the particular patient for corresponding parameters of a subset of fewer than all parameters available from the EMR system. The particular display device presents at least a first most recent value of related parameters in the subset according to a first arrangement without human intervention.

In various other embodiments, an apparatus, a system or a computer-readable storage medium is configured to perform one or more steps of the above methods.

BRIEF DESCRIPTION OF THE DRAWINGS

The present invention is illustrated by way of example, and not by way of limitation, in the figures of the accompanying drawings and in which like reference numerals refer to similar elements and in which:

FIG. 7 is a block diagram that illustrates a computer system upon which an embodiment of the invention may be implemented.

DETAILED DESCRIPTION

Figure 1:
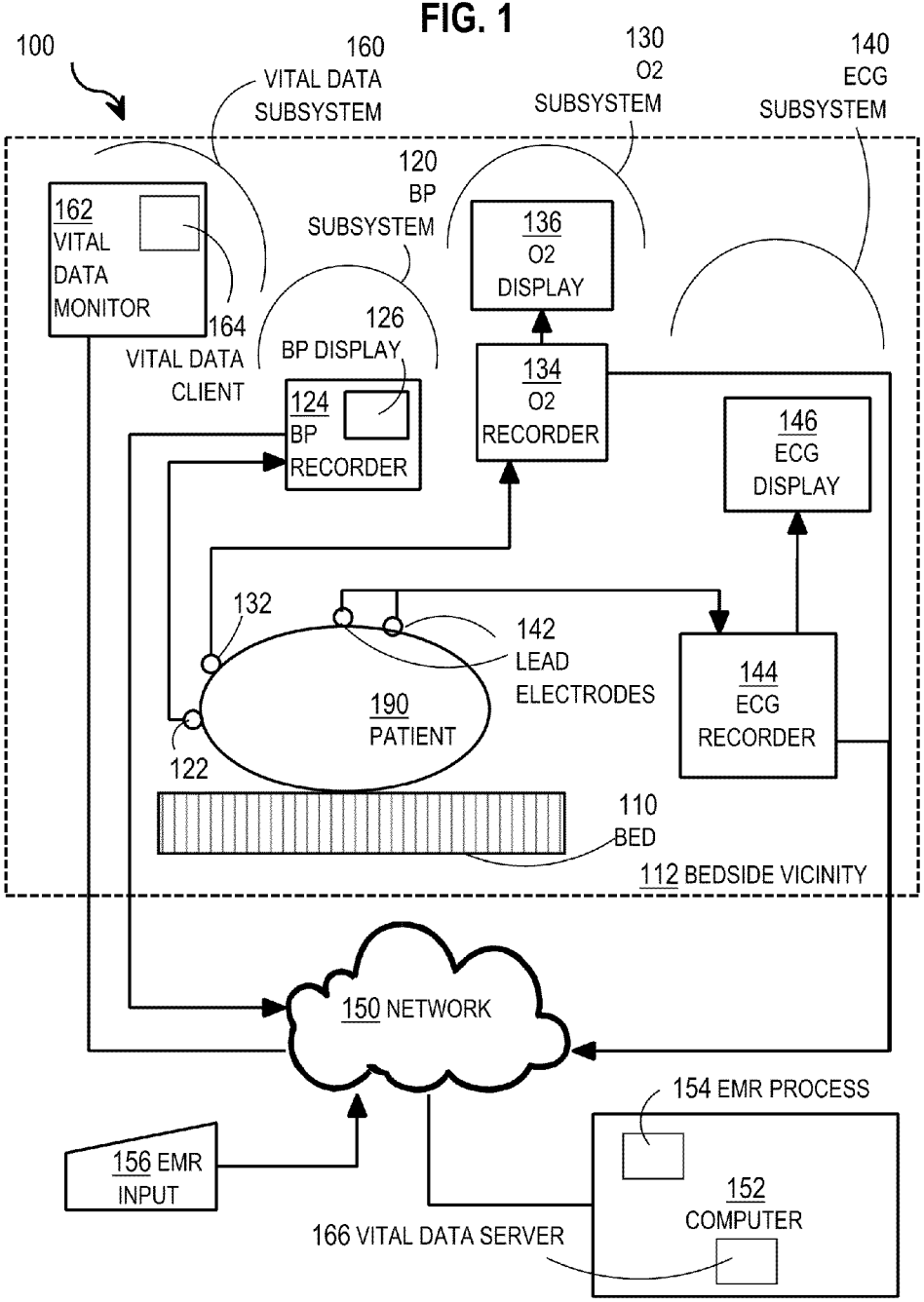
FIG. 1 is a block diagram that illustrates an example system for presenting vital data at a patient's bedside without human intervention, according to an embodiment.

Techniques are described for presenting patient data at the patient's bedside. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of client server communications between general purpose processors on a network in a hospital for patients that stay in the hospital. However, the invention is not limited to this context. In other embodiments, one or more special purpose devices communicate according to the same or different models in one or more of the same or different health care facilities that maintain an electronic medical record system for patients that stay in the facility or reside outside the facility.

1. NETWORK OVERVIEW

Networks of general purpose computer systems and special purpose devices connected by external communication links are well known. The networks often include one or more network devices that facilitate the passage of information between the computer systems. A network node is a network device, special purpose device or computer system connected by the communication links. Information is exchanged between network nodes according to one or more of many well known, new or still developing protocols. In this context, a protocol consists of a set of rules defining how the nodes interact with each other based on information sent over the communication links.

The client-server model of computer process interaction is also widely known and used in commerce. According to the client-server model, a client process sends a message including a request to a separate server process, and the server process responds by providing a service. The server process may also return a message with a response to the client process. Often the client process and server process execute on different computer devices, called hosts, and communicate via a network using one or more protocols for network communications. Network nodes are often hosts for client and server processes. The term "server" is conventionally used to refer to the process that provides the service, or the host on which the process that provides the service operates. Similarly, the term "client" is conventionally used to refer to the process that makes the request, or the host on which the process that makes the request operates. As used herein, the terms "client" and "server" refer to the processes, rather than the hosts, unless otherwise clear from the context. In addition, the server process can be broken up to run as multiple processes on multiple hosts (sometimes called tiers) for reasons that include reliability, scalability, and redundancy.

2. BEDSIDE NETWORK NODES

FIG. 1 is a block diagram that illustrates an example system 100 for presenting vital data at a patient's bedside without human intervention, according to an embodiment. Although a patient 190 is shown disposed on a bed 110 for purposes of illustration, the patient 190 is not part of the system 100. The bed 110 supports a patient 190, when present. The bedside vicinity 112, in which both the patient and other items can be viewed simultaneously, is indicated by the dashed rectangle.

The system 100 includes the bed 110, a blood pressure (BP) subsystem 120, an oxygen gas (O2) subsystem 130, an electrocardiogram (ECG) subsystem 140, a network 150, an electronic medical records (EMR) input device 156, a computer 152, and a vital data subsystem 160.

The blood pressure (BP) subsystem 120 includes a BP sensor 122, a BP recorder 124 and a BP display 126 that presents data that indicates the blood pressure of patient 190, when present and connected to sensor 122. Data indicating the patient's blood pressure originates at the sensor 122 connected to the patient 190 and travels to the BP recorder 124, where symbols representing the data are presented on display 126. Patient data does not flow in the opposite direction, so the single direction of data flow is indicated by the arrowheads on the connection between sensor 122 and recorder 124. In the illustrated embodiment, the display 126 is integral to the recorder 124, but in some embodiments the display is a separate device.

The oxygen gas (O2) subsystem 130 includes an O2 sensor 132, an O2 recorder 134 and an O2 display 136 that presents data that indicates the oxygen gas saturation level of patient 190, when present and connected to sensor 132. Data indicating the patient's oxygen gas saturation level originates at the sensor 132 connected to the patient 190 and travels to the O2 recorder 134, and symbols representing the data are presented on display 136. Patient data does not flow in the opposite direction, so the single direction of data flow is indicated by the arrowheads on the connection between sensor 132, recorder 134, and display 136. In the illustrated embodiment, the display 136 is separate from the recorder 134, but in some embodiments, the display is an integral part of the recorder.

The electrocardiogram (ECG) subsystem 140 includes a set of ECG sensors called lead electrodes 142, an ECG recorder 144, and an ECG display 146 that presents data that indicates the electrical signature of a beating heart in patient 190, when present and connected to lead electrodes 142. Data indicating the patient's heart electrical signature originates at the lead electrodes 142 connected to the patient 190 and travels to the ECG recorder 144; and trace lines and symbols representing the data are presented on display 146. Patient data does not flow in the opposite direction, so the single direction of data flow is indicated by the arrowheads on the connection between electrodes 142, recorder 144, and display 146. In the illustrated embodiment, the display 146 is separate from the recorder 144, but in some embodiments the display is an integral part of the recorder.

In a medical facility with an electronic medical record (EMR) system, an EMR process 154 executes on computer 152 connected to network 150. The network is any local area network (LAN), or wide area network (WAN) well known in the art, with wired communication links or wireless communication links or both. The network 150 and computer 152 reside outside the bedside vicinity 112. The EMR process 154 may operate on one or more computers or special purpose devices connected to network 150. The EMR process 154 includes data structures (not shown) that store all data for every patient in the facility and may include data for patients in a different facility as well. Some patient data, such as patient identification data and medications and laboratory orders and results, is manually input via an EMR input device 156 (e.g., a keyboard or optical scanner at a computer terminal) and passed directly (not shown) to computer 152 or indirectly through network 150 (as shown). The EMR input device is typically outside the bedside vicinity 112, as shown in FIG. 1.

Data flows from the vital signs recorders 124, 134 and 144 through the network 150 to the EMR process 154 on computer 152, as indicated by the arrowheads on the connections from the recorders 124, 134, 144 to network 150. The vital signs data is stored by the EMR process 154 in association with other data for the same patient. Any data in the EMR system can be retrieved by a human user, as described in the background section, by sitting at a terminal, such as EMR input device 156, and remotely operating the EMR process 154 to request the data for a patient of interest and a time of interest. Typically the requested data is returned in spreadsheet format depicted on a display screen (not shown) associated with the input device 156 and connected to network 150, or printed out on a network printer (not shown) also connected to network 150.

According to an illustrated embodiment, the system includes a vital data subsystem 160. The vital data subsystem 160 includes a vital data monitor 162 located within the bedside vicinity 112, and a process executing on a network computer, such as vital data server 166 executing on computer 152. The vital data monitor 162 is a display device. In the illustrated embodiment, the vital data monitor includes a vital data client 164 executing on a general purpose processor or special purpose circuit block inside the monitor 162. In some other embodiments, some or all of the vital data client executes on another special purpose or general purpose device (not shown) connected to the monitor 162 directly or connected indirectly via network 150.

As described in more detail below, the vital data monitor 162 automatically displays a subset of the information in the EMR system for the patient 190 in bed 110 in the same bedside vicinity 112 as the monitor 162. In the illustrated embodiment, the subset is that portion of the data in the EMR system that is critical to the immediate care of the patient in bed 110 by a caregiver, such as a physician making rounds alone or with one or more accompanying persons, such as interns or other physicians. Presentation styles may be specified in some embodiments by an algorithm that selects parameters to be displayed based on prioritization of interest, the number of data available, and the patterns of changes in the data.

Because the subset is automatically displayed, it is visible to the caregiver immediately upon entering the bedside vicinity, without one or more of the disadvantages of prior art retrievals from an EMR system. Thus other trained staff need not spend time retrieving the data and transferring it to paper and reading it aloud. The caregiver need not try to decipher a spoken word that passes in an instant amid distractions and audio noise.

In some embodiments, the presence of monitor 162 makes superfluous separate display devices dedicated to the vital signs recorders. Thus, in some embodiments, separate display devices for the vital signs recorders, such as O2 display 136 and ECG display 146 depicted in FIG. 1, are removed from the bedside vicinity 112.

In some embodiments, the vital data monitor 162 includes an input device such as a physical or virtual keyboard or a touch screen, so that a human user can influence or override the automatically displayed vital data. In some embodiments, the vital data monitor 162 is configured for high reliability, such as by preventing any process (e.g., software viruses or worms) other than vital data client 164 from executing, or by including special hardware (e.g., hardened electrical circuits, thermal and mechanical isolation, and backup power).

Although system 100 is depicted with a certain number of subsystems, networks, input devices and computers for purposes of illustration, in other embodiments the system includes more or fewer or the same number of one or more subsystems, networks, computers or input devices.

3. METHOD FOR PRESENTING VITAL DATA AT PATIENT'S BEDSIDE

Any process may be used to present automatically a subset of data from the EMR system at the vital data monitor 162. In an illustrated embodiment, a vital data client 164 executes on a general purpose processor inside the monitor 162 and communicates via network 150 with a vital data server 166. In other embodiments, one or more or all steps performed by the client 164 and server 166 is performed by the other process or by a third process, executing on a host anywhere on network 150.

3.1. Method at Bedside Client

Figure 2:
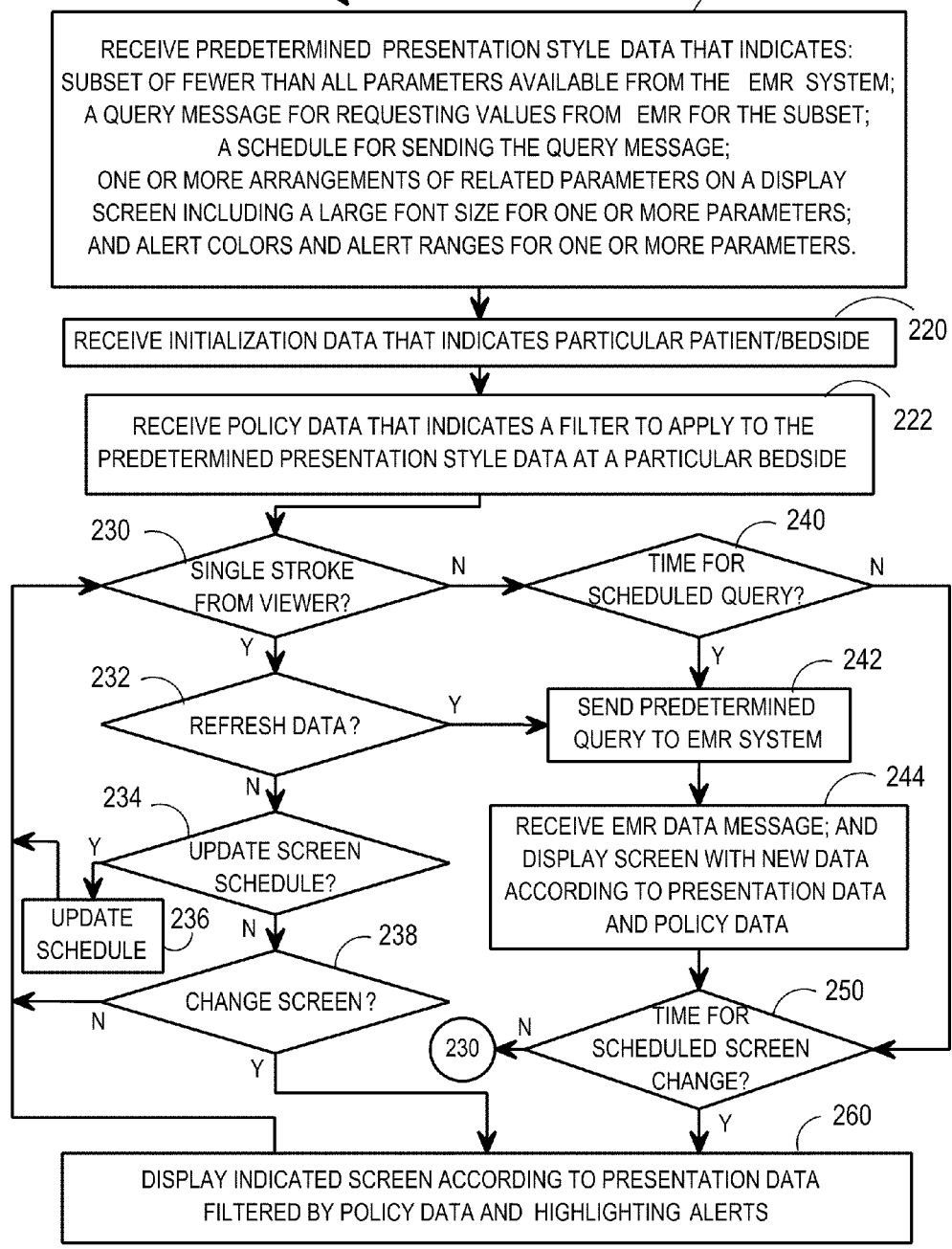
FIG. 2 is a flow diagram that illustrates at a high level a method at a client process in a display device at a patient's bedside, according to an embodiment.
Figure 3:
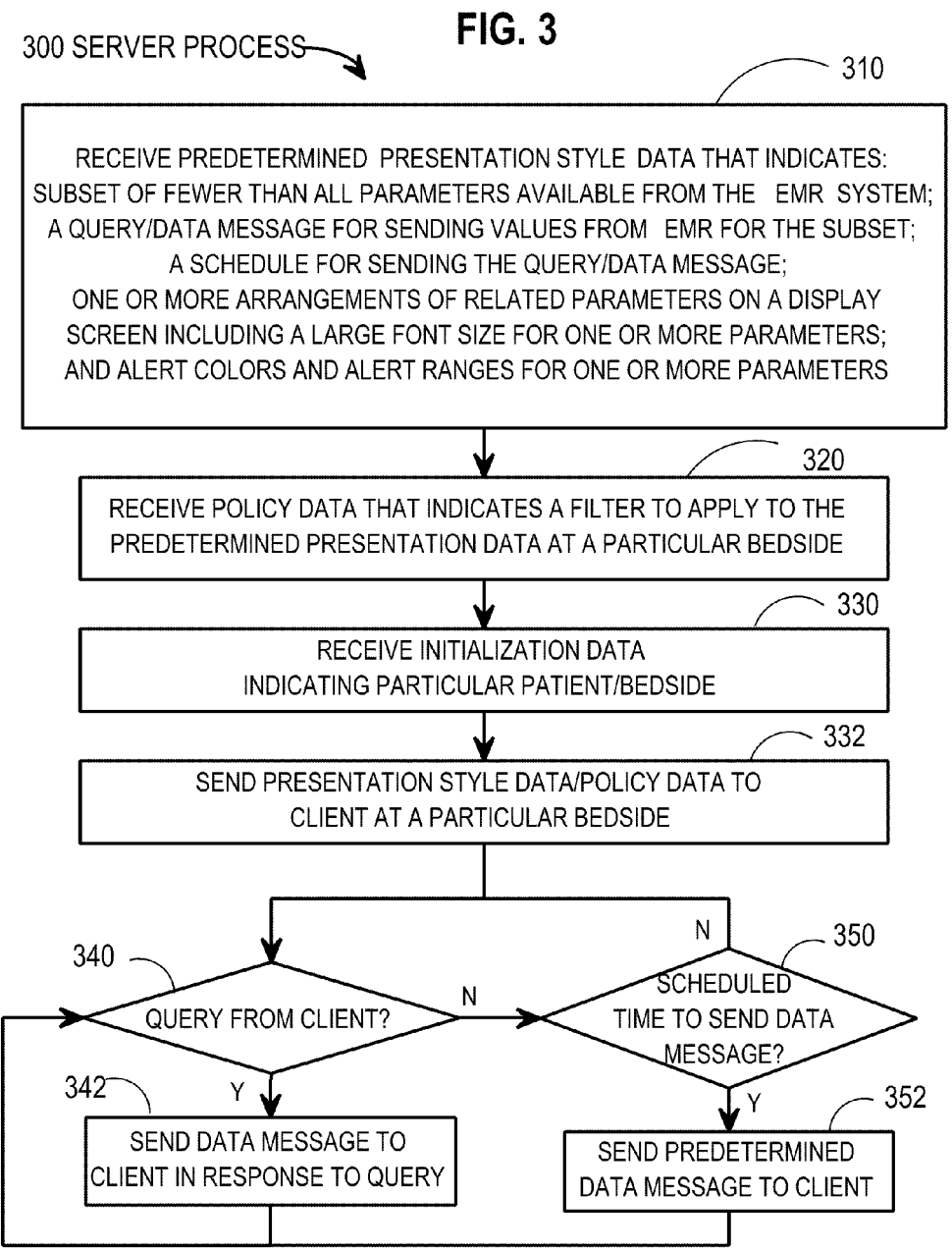
FIG. 3 is a flow diagram that illustrates at a high level a method at a server process remote from a display device at a patient's bedside, according to an embodiment.

FIG. 2 is a flow diagram that illustrates at a high level a method 200 at a client process (such as client 164) in a display device at a patient's bedside, according to an embodiment. Although steps in FIG. 2 and subsequent flow chart, FIG. 3, are shown in a particular order for purposes of illustration, in other embodiments, one or more steps may be performed in a different order or overlapping in time, in series or in parallel, or one or more steps may be omitted or added, or changed in some combination of ways.

In step 210, predetermined presentation style data is received. The presentation style data indicates what parameters from the EMR system are to be received and how the values for those parameters are to be presented on a display.

Any method may be used to receive this data. For example, in various embodiments, the data is included as a default value in software instructions, is received as manual input from a network administrator on the local or a remote node, is retrieved from a local file or database, or is sent from a different node on the network, either in response to a query or unsolicited, or the data is received using some combination of these methods.

In the illustrated embodiment, the predetermined presentation style data indicates a query message for retrieving data from the EMR system and a schedule for sending the query message. In some embodiments, the query message is formatted according to the EMR system and directed to the EMR process 154 already resident on a computer 152 connected to network 150. In some of these embodiments, vital data server 166 is omitted. In some embodiments, the query requests all data for a particular patient for a particular time interval. In some embodiments, the query requests only data for the subset of parameters for a particular patient for a particular time interval. The schedule for sending the query message indicates when or how often to send the query. For example, it is assumed for purposes of illustration that the schedule indicates the query should be sent every 30 minutes at a random delay after the start of an hour so that requests for all patients are not sent at the same time to the vital data server 166 or EMR process 154.

In some embodiments, the data is sent automatically from a vital data server 166 and the query message or the schedule or both are omitted from the predetermined presentation style data.

In the illustrated embodiment, the predetermined presentation style data indicates one or more arrangements of related parameters. Applicants have recognized that it is an advantage for the data from the EMR records to be grouped differently than the data is sent by the EMR system in response to a query. For example, all items of information retrieved from the EMR system are presented in time order, even if those items are not related to each other. Applicants prefer to arrange the data for a particular biological system on the same display at the same time. Thus, in some embodiments, the predetermined presentation data indicates multiple arrangements (called screen views hereinafter, although the display device need not be limited to a screen). For example, one screen view is used to present current values for parameters associated with the patient's cardio vascular system (CVS), and a second different screen view is used to present current values for parameters associated with the patient's respiratory system, and a still different third screen view is used to present current values for parameters associated with the medications currently being administered to the patient, and so on. For example, another view presents current medications (cancelled, ordered, dangerous, etc); and another view displays current cultures results (positive, negative, pending); and another view presents checklists of order sets or intended tasks and goals. A particular embodiment of multiple screen views is described in more detail in a later section with reference to FIG. 4, FIG. 5 and FIG. 6.

In some embodiments in which multiple arrangements are indicated, the predetermined presentation style data also indicates a screen change schedule that indicates how long to display each screen view, or what order to cycle through one or more of the multiple screen views, or both.

In some embodiments, the arrangement indicated by the predetermined presentation style data includes a font size for one, more or all parameters to be displayed in a screen view. In a preferred embodiment, at least one font size is large enough so that one or more persons, such as caregivers, viewing the display can discern the values presented at a distance from about 5 feet (1.5 meters) to about 12 feet (4 meters) apart from the display device. Thus, in some embodiments, predetermined presentation style data indicates an arrangement that includes a font size for a parameter such that a value of the parameter is visible on the display device to multiple viewers more than five feet from the display device.

In some embodiments, the arrangement indicated by the predetermined presentation style data includes one or more alert colors to distinguish a normal and stable value from a value trending toward an abnormal range or in a dangerous range. In some embodiments, two different colors distinguish values that are trending larger or toward dangerous from values that are trending smaller or toward normal, either in the normal range, or in the dangerous range, or between the normal and dangerous ranges. In some of these embodiments, the indicated arrangement includes ranges to associate with normal, abnormal and dangerous. Thus a most recent value in a particular arrangement is presented in one color to indicate whether the most recent value is a normal and stable value or a value trending toward an abnormal range or in a dangerous range. A particular embodiment of multiple alert colors is described in more detail in a later section with reference to FIG. 4, FIG. 5 and FIG. 6.

In step 220, initialization data is received that indicates a particular patient or bedside or both. In order to process queries, the recipient of the query must know what patient or bedside is the object of the query. In some embodiments, a network administrator uses an input device associated with the monitor to input a bed identifier (ID), such as a room number (combined with a bed number for multiple beds in the same room) to the vital data monitor during step 220. When a patient is admitted to the facility and given a patient identifier, the patient is assigned to a free bed and the patient and bed are associated in the EMR system. Thus it is sufficient for the client process 164 on the vital data monitor to identify the bed ID in a query and retrieve the most recent values for the patient associated in the EMR system with the particular bed having that bed ID.

In some embodiments, a network administrator obtains the media access control (MAC) number, which is unique among all network devices, for the vital data monitor 162 and inputs this number in association with the bed identifier into either the EMR system or into the vital data server 166 process on computer 152. The vital data server 166 sends the bed identifier or patient identifier in a message directed to the MAC address of the vital data monitor 162, and that message is received during step 220.

In some embodiments, the vital data monitor 162 is simply plugged into a network interface port, such as a data port, associated with the bed 110 in a room. The network data that associates the MAC address of the vital data monitor 162 with that network port is used by the vital data server 166 to associate the MAC address of the vital data monitor 162 to the bed 110 and the associated patient. The vital data server 166 sends the bed identifier or patient identifier in a message directed to the MAC address of the vital data monitor 162, and that message is received during step 220.

In some embodiments, the vital data server 166 determines the association between the MAC address of the vital data monitor 162 and the bed 110 or patient 190 based on the network interface port, as described above; but does not send a message to the vital data client 164, and thus step 220 is omitted. The client simply uses its own MAC address as an identifier for the particular bed/patient for which data is requested from the EMR system and sends the query to the vital data server 166. The vital data server 166 translates the MAC address in the query to the patient/bed identifier used in the EMR system.

In step 222 policy data is received. The policy data indicates an alteration to a value for a particular parameter in the subset before presentation. For example, the policy data indicates certain parameters that should not be displayed or parameters that should be combined in a different arrangement than the arrangement in the predetermined presentation style data. Thus, a most recent value corresponding to the particular parameter indicated in the policy data is altered before presenting the most recent value according to an arrangement. This feature is useful for filtering data for privacy and security (e.g., blocking out private patient information when the bedside vicinity 112 is viewed by visitors not authorized to know the patient). This feature is also useful for modifying the predetermined presentation style data dynamically (e.g., moving values for one or more parameters from one screen view to another, or changing font size or alert ranges), or tailoring the arrangement for individual patients (e.g, for heart transplant patients or kidney transplant patients or trauma victims or children or infants).

Control then passes to an automatic loop represented by steps 230 through 260.

In step 230, it is determined whether a bedside human user (called a viewer herein) has entered input to override or change the automatic presentation of the subset of EMR data (e.g., the automatic presentation of vital data). To avoid the deficiencies of prior art approaches, it is desirable that the user input be optional, simple and swift. Thus, in the illustrated embodiment, the viewer input is represented by a single stroke, such as a single touch of the touch screen or pressing a single key of a physical or virtual keyboard or producing a single click on a pointing device. If there is no input from a viewer, then control passes to step 240. Usually there is no viewer input and control passes to step 240.

In step 240, it is determined whether it is time for a scheduled query. If so, control passes to step 242. In step 242, a query message indicated by the predetermined presentation style data is sent to the EMR system, either directly to EMR process 154, or indirectly, though the vital data server 166. Control then passes to step 244.

In step 244, an EMR data message is received that includes data from the EMR system. In some embodiments, the data message is received directly from the EMR process 154; in other embodiments, the data message is received indirectly through the vital data server process 166. Control passes from step 244 to step 250.

In the illustrated embodiment, step 244 includes displaying the screen view with the new data according to an arrangement indicated in the presentation style data altered according to the policy data, if any. As described above, the corresponding arrangement includes a large font for viewing one or more values being presented at a distance of five feet or more and an appropriate alert color depending on the value and the alert ranges. As used herein, the alert ranges include a normal range with a neutral color (e.g., white), a dangerous range with a color indicating danger (e.g., red) and an abnormal range with one or more colors (e.g., green and yellow) indicating a value between the normal range and the dangerous range, if any. For example, in some embodiments, green indicates a value in an abnormal range but trending toward the normal range; and yellow indicates a value in an abnormal range but trending toward the dangerous range.

In some embodiments, the screen view is not changed upon receipt of the new data but is displayed in turn according to the current screen change schedule. For example, in some embodiments with multiple screen views, the display is not updated upon receipt of a new data message, but is displayed in the course of the current screen change schedule. In some embodiments with only one screen view, the screen is displayed in step 244 upon receipt of a new data message.

In some embodiments, a data message is received automatically from a vital data server 166, and the vital data client 162 does not send a query message on a schedule. In these embodiments, step 240 is omitted; and control passes from step 230 directly to step 244, described above.

Control passes from step 244 to step 250. In step 250, it is determined whether it is time for a scheduled screen change according to the current screen change schedule. If not, control passes back to step 230, described above. For example, in some embodiments with only one screen view, or with a default screen that is displayed unless and until the viewer makes a different selection, control passes to step 230.

If it is determined in step 250 that it is time for a scheduled screen change according to the current screen change schedule, then control passes to step 260. In step 260 the indicated screen view (e.g., the next in the predetermined order) is displayed automatically according to a corresponding arrangement indicated in the predetermined presentation style data, but altered according to the policy data, if any. As described above, the corresponding arrangement includes a large font for one or more values being presented and an appropriate alert color depending on the value and the alert ranges. Control then passes back to step 230.

If it is determined in step 230 that a viewer has entered input to override or change the automatic presentation of the subset of EMR data, then control passes to step 232. In step 232 it is determined whether the viewer input indicates that data is to be refreshed. If so, then control passes to step 242 to send a query for EMR data. As described above, in step 242, a query message indicated by the predetermined presentation style data is sent to the EMR system, either directly to EMR process 154, or indirectly, though the vital data server 166. Control then passes to step 244 and following steps as described above.

If it is determined in step 232 that the viewer input does not indicate that data is to be refreshed, then control passes to step 234. In step 234 it is determined whether the viewer input indicates that the current screen change schedule is to be updated. If so, then control passes to step 236. In step 236, the screen change schedule is updated to speed up or slow down the rate of changing from one screen view to another based on the user input. In some embodiments, the rate of changing from one screen view to another is changed according to a value indicated by the viewer input (e.g., a numeric value or value on a pull down menu or an icon indicated by the touch screen input). In some embodiments two icons on a touch screen are provided for indicating how to update the screen change schedule; one icon indicates speeding up the rate of change, and the other icon indicates slowing down the rate of change. The rate of changing from one screen view to another is updated by a fixed percentage (e.g., 20%) every time the viewer strikes one of the icons. Control then passes back to step 230.

In some embodiments, the update to the screen change schedule is retained until a viewer again updates it. In some embodiments, the screen change schedule reverts to the value indicated in the predetermined presentation style data after a certain amount of time (e.g., 30 minutes).

If it is determined in step 234 that the viewer input does not indicate that the current screen change schedule is to be updated, then control passes to step 238. In step 238 it is determined whether the viewer input indicates that a different screen is to be displayed. If not, control passes back to step 230. If so, then control passes to step 260, described above, to display the indicated screen according to a corresponding arrangement indicated in the predetermined presentation style data but altered according to the policy data, if any.

Any method may be used to determine that the user input indicates a particular screen. In some embodiments, the screen to display is indicated by the user input (e.g., a numeric value or value on a pull down menu or an icon indicated by the touch screen input). In some embodiments two icons on a touch screen are provided for indicating the next screen to display, one icon indicates the next screen in the predetermined order and the other icon indicates the previous screen in the predetermined order. In some embodiments, the indicated screen view is displayed until the viewer indicates a different screen view. In some embodiments, the monitor reverts to the current screen change schedule after a certain amount of time (e.g., 2 minutes).

3.2. Method at Remote Server

FIG. 3 is a flow diagram that illustrates at a high level a method 300 at a server process remote from a display device at a patient's bedside, according to an embodiment.

In step 310, predetermined presentation style data is received. The presentation style data indicates what parameters from the EMR system are to be received at the bedside display device and how the values for those parameters are to be presented on a display there. In the illustrated embodiment, the predetermined presentation style data is sent to the vital data client 164 from the vital data server 166 and thus includes presentation style data used by both client 164 and server 166. In some embodiments, the vital data client 164 obtains its presentation style data from another source and the presentation style data received at the vital client server 166 is greatly reduced to just the data used by the server. For example, the data used just at the server includes the subset of parameters used by the vital data subsystem 160, a data message and data message schedule for sending the most recent values from the server 166 to the client 164, and a EMR query message for obtaining at the server 166 the most recent values for the subset from the EMR system. Any method may be used to receive the predetermined presentation style data, as described above.

In the illustrated embodiment, the vital data client 164 does not send a query message directly to the EMR process 154, but instead sends a request for the most recent values to the vital data server 166 or sends no queries at all. In these embodiments, the vital data server 166 sends a query message formatted according to the EMR system to the EMR process 154 to request all the most recent values for the parameters in the subset of vital data parameters.

The schedule for sending the query/data message indicates when or how often to send the query/data message. For example, it is assumed for purposes of illustration that the schedule indicates a data message should be sent from the server 166 to the client 162 every 30 minutes at a random delay after the start of an hour so that data messages for all patients are not sent at the same time from the vital data server 166.

In the illustrated embodiment, the predetermined presentation style data indicates one or more arrangements of related parameters, as described above.

In step 320 policy data is received. The policy data indicates an alteration to a value for a particular parameter in the subset before presentation, as described above. Different policy data for different patients is received at the server 166 in some embodiments.

In step 330, initialization data is received that indicates an association between a particular client 164 and a particular patient or bedside or both. In some embodiments, a network administrator obtains the MAC number of the vital data monitor 162, and inputs this number in association with the bed identifier. In some embodiments, the vital data server 166 sends the bed identifier or patient identifier in a message directed to the MAC address of the vital data monitor 162 during step 330. In some embodiments, the network data that associates the MAC address of the vital data monitor 162 with a network port is used by the vital data server 166 to associate the MAC address of the vital data monitor 162 to the bed 110 and the associated patient. The vital data server 166 sends the bed identifier or patient identifier in a message directed to the MAC address of the vital data monitor 162, during step 330. In some embodiments, the vital data server 166 determines the association between the MAC address of the vital data monitor 162 and the bed 110 or patient 190 based on the network interface port, as described above; but does not send a message to the vital data client 164. The vital data server 166 translates the MAC address in a query from the client 164 to the patient/bed identifier used in the EMR system.

In step 332 the presentation style data and policy data, if any, are sent to the vital data client 164 on the vital data monitor 162. In some embodiments, the client receives the presentation style data and policy data independently of the server 166; and step 332 is omitted.

Control then passes to an automatic loop represented by steps 340 through 352.

In step 340, it is determined whether a query for most recent values is received from a vital data client 164. If so, control passes to step 342. In step 342, a data message is sent to the vital data client in response to the query. In some embodiments, step 342 includes sending a EMR formatted query to the EMR process 154 for the most recent value or values for each of one or more or all parameters in the subset of parameters for the vital data subsystem for the particular patient. In some embodiments, this step includes translating a MAC address of the monitor 162 hosting client 164 into a bed number or patient identifier for use in the EMR query. During step 342 in such embodiments, a response is received from the EMR system with the values for the requested parameters. In some embodiments, all EMR data for the patient is received. In some embodiments, only values for the subset are received. The data message with the most recent value or values for each of the subset of parameters is generated based on the response from the EMR system.

If it is determined, in step 340, that a query for most recent values is not received from a vital data client 164, then control passes to step 350. In step 350, it is determined whether it is a scheduled time to send a data message. If not, control passes back to step 340.

If it is determined, in step 350, that it is a scheduled time to send a data message, then control passes to step 352. In step 352, a data message is sent to the vital data client, as described above for step 342.

In some embodiments, the vital data client 164 does not generate queries. In such embodiments, steps 340 and 342 are omitted and control passes from step 332 to step 350, and from step 352 to step 350.

4. EXAMPLE EMBODIMENTS

Figure 4:
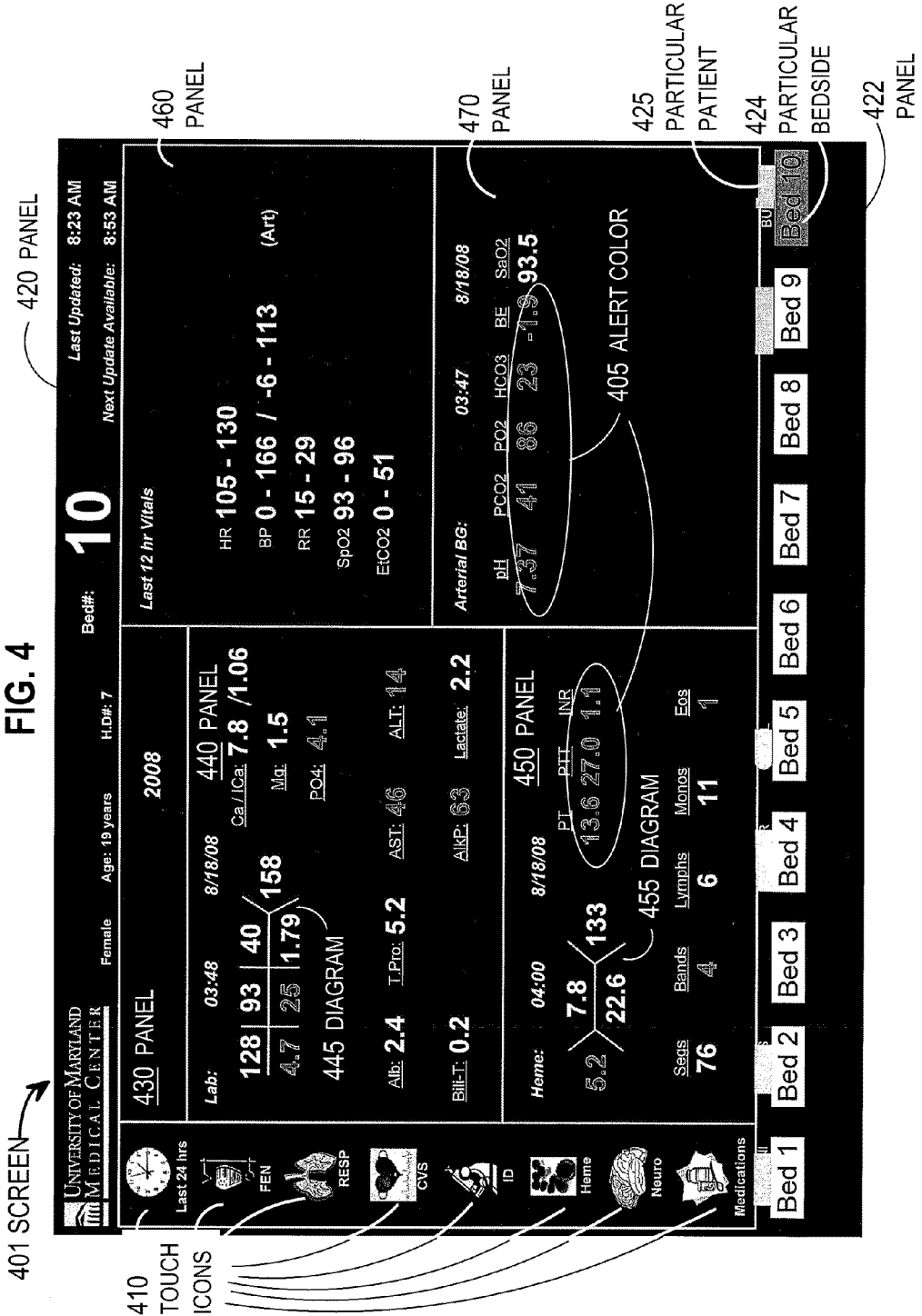
FIG. 4 is a block diagram that illustrates an example arrangement of EMR parameter values displayed automatically at a patient's bedside, according to an embodiment.

FIG. 4 is a block diagram that illustrates an example arrangement 401 of EMR parameter values displayed automatically at a patient's bedside, according to an embodiment. In the illustrated embodiment, the display device is a touch screen sensitive to user input by detecting a location where a user touches the screen, as is well known in the art. This arrangement 401 is designated hereinafter default screen view 401. According to the illustrated embodiment, the most recent values of related parameters available from the EMR system are grouped into one or more panels. Default screen view 401 includes: touch icons 410; first context panel 420; screen change rate panel 422; second context panel 430; fluids, electrolytes, nutrition (FEN) panel 440; hemoglobin (HEME) panel 450; vital signs panel 460; and respiratory (RESP) panel 470.

Touch icons 410 are used by a viewer to selected eight different detailed screen views, as described in more detail below. The eight different detailed screen views indicated by the touch icons 410 include, in order from top to bottom, a last 24 hours screen view, a FEN screen view, a RESP screen view, a cardiovascular system (CVS) screen view, an infectious disease (ID) screen view, a HEME screen view, a neurological system (NEURO) screen view, and a medications screen view. The default screen view 401 includes multiple panels that each displays the most recent values for a portion of the parameters on one or more of the eight detailed screen views.

First context panel 420 includes a logo for the facility (e.g., University Medical Center), values for patient demographic parameters (gender, age, identification number), a bed identifier (e.g., 10) in large font easily discerned by multiple viewers five feet or more from the display device, a time when the data was last updated (e.g., 8:23 AM) and a time when the next update is scheduled (e.g., 8:53 AM). The second context panel 430 includes additional information, such as the patient's name (redacted) and a date (partially redacted).

In the illustrated embodiment, the screen change rate panel 422 includes bed icons that are used by a viewer to select screens for a bed on which the most recent values are presented by touching the corresponding icon. For example, the touch icon 424 for particular bed 10 is highlighted, as is a label 425 for a particular patient associated with the bed. In another embodiment, the bed icons are replaced by icons that are touched to control the cycling rate among one or more screen views for a particular bed and associated patient, as described above. For example, one icon is touched to indicate that data is to be refreshed by querying the EMR system, a different icon is touched to indicate that the current screen change schedule is to be updated, or one of a set of icons is touched to indicate a particular value for the rate of changing from one screen view to another. In some embodiments two icons in screen change rate panel 422 are provided to indicate speeding up the rate of screen changes, or slowing down the rate of screen changes, respectively, as described above.

The FEN panel 440 includes a lab time and date, a diagram 445 of standard FEN parameter values familiar to clinicians, as well as labeled values for other parameters. The diagram 445 lists the values top row (left to right), bottom row (left to right), and right most, respectively: Sodium (mmol/L), Chloride (milliMoles per liter, mmol/L), BUN (milligrams per deciliter, mg/dL), Potassium (mmol/L), CO2 (mmol/L), Creatinine (milligrams per deciliter, mg/dL), Glucose (mg/dL). Elsewhere in panel 440 are presented Calcium (mg/dL), Ionized Calcium (mmol/L), Magnesium (mg/dL), Phrosphate (mg/dL). In the rest of the panel: Alb=Albumin (grams per deciliter, g/dL), T.Pro=Total protein (g/dL), AST (units/L), ALT (units/L), Bili-T=Bilirubin Total (mg/dL), AlkP=Alkaline Phosphatase (units/L), Lactate (mmol/L), LDH (units/L). The font size of the values are large so as to be read at a distance, e.g., at five to twelve feet. The colors of some values are changed from white (for normal stable values) to another alert color for values in a range of abnormal or dangerous values.

The hemoglobin (HEME) panel 450 includes a lab time and date, a diagram 455 of standard HEME parameter values familiar to clinicians, as well as labeled values for other parameters. The diagram 455 lists the values (in order left/top/bottom/right, respectively) of: white blood cell count (thousands/L), hemoglobin (g/dL), hematocrit (%), platelet (thousands/mcL). Other displayed parameters and associated values include PT=protime (sec), PTT=Prothrobin Time (sec), INR=International Normalized Ratio (no unit), Segs=semented neutrophils (%), Bands (%), Lymphs=Lymphocytes (%), Monos=Monocytes (%), Eos=Eosinophils (%). The font size of the values are large so as to be read at a distance, e.g., at five to twelve feet. The colors of some values are changed from white (for normal stable values) to another alert color for values in a range of abnormal or dangerous values. For example, items enclosed by an oval indicate values presented in an alert color 405. In some embodiments the alert colors are: red=critical values (low or high), pink=above normal reference range but below critical high value, yellow=below normal reference range but above critical low value.

The vital signs panel 460 includes a label indicating the values presented are for the "Last 12 hr Vitals," i.e., vital signs for the last 12 hours, as well as labeled values for vital signs parameters. In panel 460, HR=heart rate (beats/minute), BP=blood pressure (mmHg_, RR=respiratory rate (rate/minute), SpO2=oxygenation saturation by pulse oximetry (%), EtCO2=end-tidal carbon dioxide (%). The font size of the values are large so as to be read at a distance, e.g., at five to twelve feet. All of the example values are in a normal range so none are in an alert color.

The respiratory (RESP) panel 470 includes a lab time and date, and labeled values for certain parameters. These labels are self evident except BE=base excess (mmol/L), pH (no unit), PCO2=partial pressure of Carbon-dioxide in blood (millimeters of Mercury, mm Hg), PO2=partial pressure of oxygen in blood (mm Hg), HCO3=bicarbonate (mmol/L), SaO2(%). The font size of the values are large so as to be read at a distance, e.g., at five to twelve feet. The colors of some values are changed from white (for normal stable values) to another alert color for values in a range of abnormal or dangerous values. For example items enclosed by an oval indicate values presented in an alert color 405.

Figure 5:
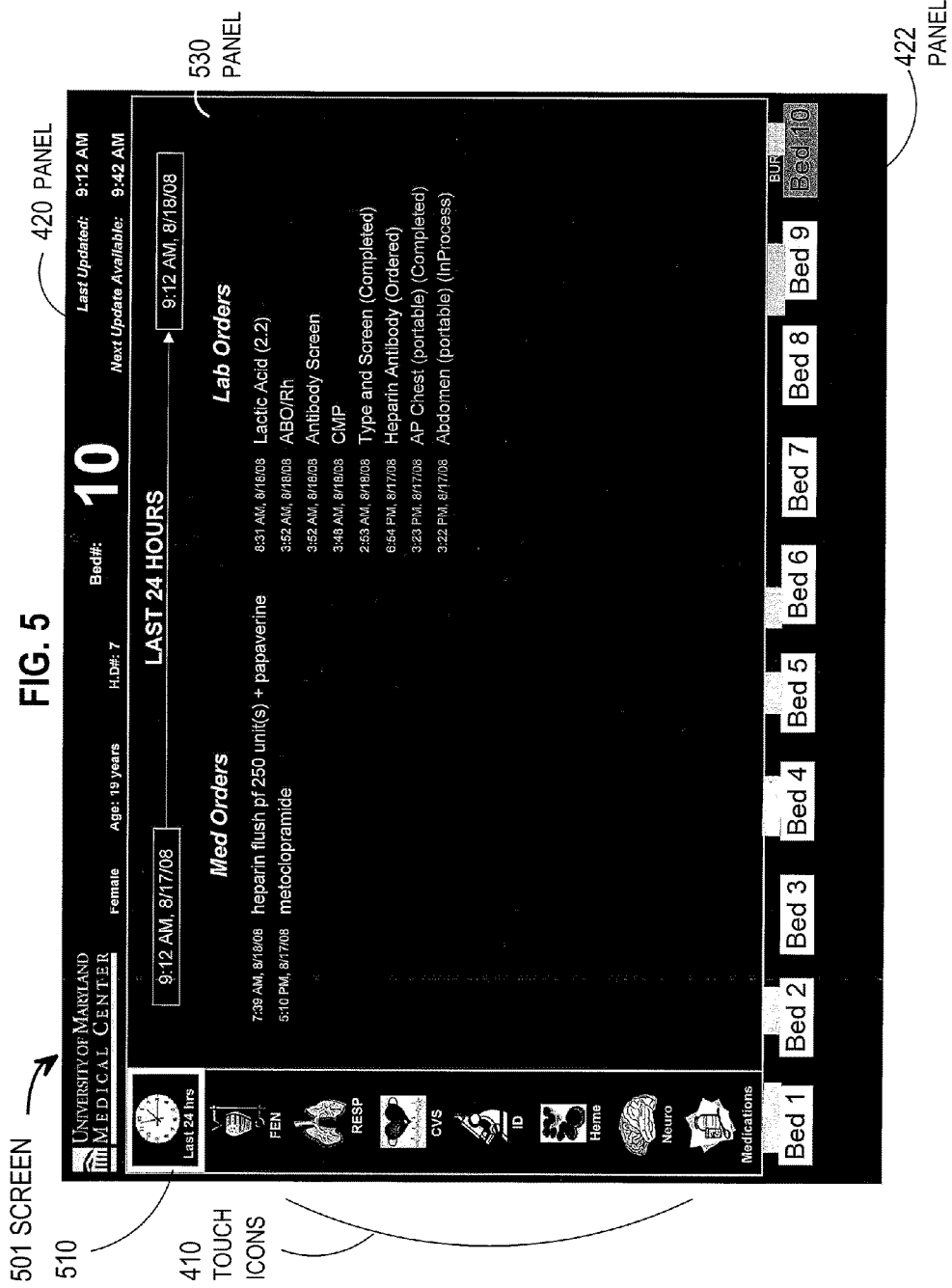
FIG. 5 is a block diagram that illustrates a different example arrangement of EMR parameter values displayed automatically at a patient's bedside, according to an embodiment.

FIG. 5 is a block diagram that illustrates a different example arrangement 501 of EMR parameter values displayed automatically at a patient's bedside, according to an embodiment. This arrangement 501 is the last 24 hours screen view 501 indicated by the top touch icon on the default screen view 401. The last 24 hours screen view 501 includes the touch icons 410, first context panel 420 and screen change rate panel 422, as described above with respect to FIG. 4. The last 24 hours screen view 501 also includes medications and lab orders panel 530. The last 24 hours touch icon 510 is highlighted to indicate that the associated detailed screen view is currently being presented.

The medications and lab orders panel 530 presents the start and stop date and time for the last 24 hours, a list the medications ordered in the last 24 hours and a list of the laboratory tests ordered in the last 24 hours. The EMR data are sorted before presentation herein to automatically display a time log of laboratory orders and medication orders as captured by EMR. For example, all medication orders are automatically displayed by categories and by time to provide an at-a-glance view of summaries of all medication orders. In the illustrated embodiment, none of the values in the panel 530 is in large font or a non-normal alert color. Even so, an advantage of the values presented in panel 530 is that a caregiver can see immediately what tests and treatments have been most recently applied to the particular patient in the same bedside vicinity as the vital data monitor 162. This assists the caregiver in determining what incremental changes might be called for, rather than coming up with a complete treatment protocol from a blank start. In other embodiments, current medication are separated into categories, e.g., cancelled, ordered, dangerous, etc. In some embodiments, current cultures results, e.g., positive, negative, pending, etc., are also presented with the lab orders column.

Figure 6:
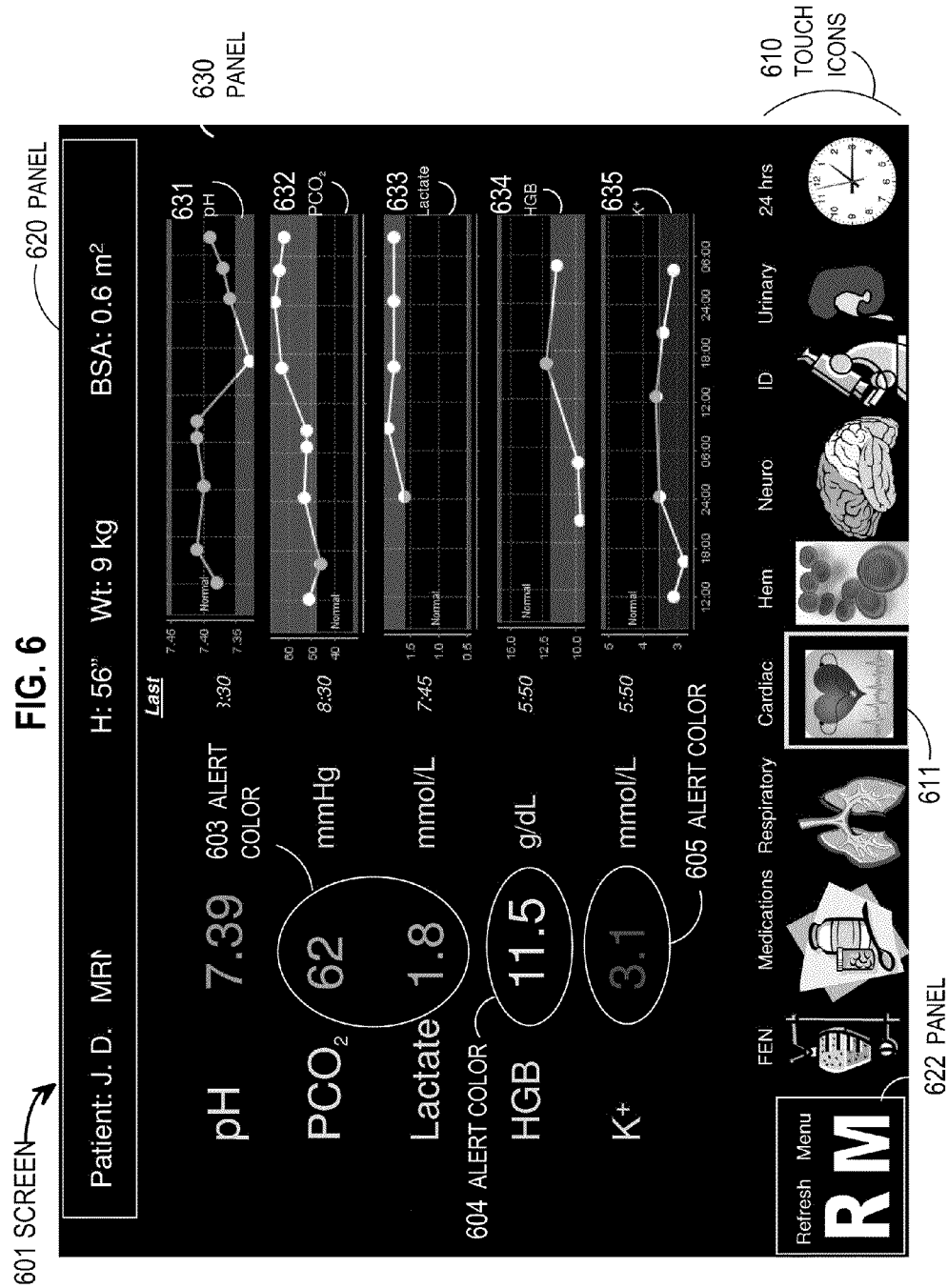
FIG. 6 is a block diagram that illustrates yet another different example arrangement of EMR parameter values displayed automatically at a patient's bedside, according to an embodiment.

FIG. 6 is a block diagram that illustrates yet another different example arrangement 601 of EMR parameter values displayed automatically at a patient's bedside, according to an embodiment. This arrangement 601 is the CVS screen view 601 similar to one indicated by the fourth touch icon on the default screen view 401. The CVS screen view 601 includes the touch icons 610 according to a different embodiment with some different names, first context panel 620 according to a different embodiment and screen change rate panel 622 according to a different embodiment. The screen change rate panel 622 includes a refresh icon "R" for requesting the latest data from the EMR, and a menu icon "M" for selecting other options, such as a change in the rate of cycling among the predefined screens. The CVS screen view 601 also includes detailed CVS panel 630. The cardiac touch icon 611 corresponds to the CVS touch icon in FIG. 4; and is highlighted to indicate that the associated detailed screen view is currently being presented.

The detailed CVS panel 630 presents the values for five parameters and the parameter symbols in large font so as to be read at a distance, e.g., at five to twelve feet. The colors of some values are changed from white (for normal stable values) to another alert color for values in a range of abnormal or dangerous values. For example values enclosed by a first oval indicate values presented in a first alert color 603 (e.g., pink for above normal) values enclosed by a second oval indicate values presented in a second alert color 604 (e.g., yellow for below normal); and, values enclosed by a third oval indicate values presented in a third alert color 605 (e.g., red for critical/dangerous). The trends over the last 12 to 48 hours for the five parameters are also shown as graph 631, graph 632, graph 633, graph 634 and graph 635 respectively. Next to each graph is a value for a time (labeled "Last") of the most recent measurement. Trend data are provided automatically when more than one value is available in a default time window (for example, 48 hours). Immediate availability of trend data provides a useful basis to interpret the current value, in relation to the historical references values.

Other parameters in other font sizes and alert colors are presented on others of the eight detailed screen views; but are not discussed further herein. The default and detailed screens already depicted are sufficient to describe how to make and use some embodiments of the invention.

5. HARDWARE OVERVIEW

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitute computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. Computer readable storage media refers to computer-readable media excluding carrier waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software, unless otherwise explicitly stated. The hardware or software or combination is referred to herein as logic encoded in tangible media.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

6. EXTENSIONS AND ALTERNATIVES

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for presenting patient data at the patient's bedside comprising:
 receiving without human intervention, at a particular display device located bedside for a particular patient, predetermined presentation style data that indicates:
  a subset of fewer than all parameters available from an electronic medical records (EMR) system;
  a first arrangement on a display device of related parameters in the subset;
 receiving at the particular display device without human intervention a plurality of most recent values from the EMR system, wherein the plurality of most recent values is associated in the EMR system with the particular patient for a corresponding plurality of parameters of the subset;

presenting, on an initial screen at the particular display device according to the first arrangement without human intervention, a first most recent value of the plurality of most recent values;

wherein receiving the predetermined presentation style data further comprises receiving predetermined presentation style data that indicates a predetermined query message and a predetermined schedule; and receiving the plurality of most recent values further comprises sending the predetermined query message to the EMR system on the predetermined schedule without human intervention and receiving at least one value of the plurality of most recent values in response to sending the predetermined query.

2. The method as recited in claim 1, wherein the subset of fewer than all parameters available from the EMR system excludes such parameters that are not critical for determining status of or treatment for the patient by a caregiver.

3. The method as recited in claim 1, wherein receiving the plurality of most recent values further comprises receiving the plurality of most recent values from the EMR system on a predetermined schedule without human intervention.

4. The method as recited in claim 1, receiving the plurality of most recent values further comprises sending the predetermined query message to the EMR system in response to a single stroke from a human user at an input for the particular display device.

5. The method as recited in claim 1, further comprising receiving initialization data that indicates a particular bedside where the particular display device is located.

6. The method as recited in claim 1, further comprising receiving initialization data that indicates the particular patient in a bed where the particular display device is located bedside.

7. The method as recited in claim 1, wherein:
the method further comprises receiving policy data that indicates an alteration to a value for a particular parameter in the subset before presentation; and
presenting the first most recent value according to the first arrangement further comprises altering the first most recent value to a second most recent value corresponding to the particular parameter based on the policy data before presenting the second most recent value according to the first arrangement.

8. The method as recited in claim 1, wherein:
the first arrangement includes a font size on the display device for a parameter of the subset, such that a value of the parameter is visible on the display device to multiple viewers more than five feet from the display device; and
presenting the first most recent value according to the first arrangement further comprises presenting the first most recent value according to the font size.

9. The method as recited in claim 1, wherein:
the first arrangement includes a plurality of colors to distinguish a normal and stable value from a value trending toward an abnormal range or in a dangerous range; and
presenting the first most recent value according to the first arrangement further comprises presenting the first most recent value in one color of the plurality of colors to indicate whether the first most recent value is a normal and stable value or a value trending toward an abnormal range or in a dangerous range.

10. The method as recited in claim 1, wherein:
receiving the predetermined presentation style data further comprises receiving predetermined presentation style data that indicates a different second arrangement on the display device of different related parameters in the subset; and
presenting the first most recent value according to the first arrangement further comprises presenting the first most recent value according to the first arrangement for a first limited time and then presenting a different second most recent value of a second parameter of the different related parameters according to the second arrangement for a second limited time.

11. The method as recited in claim 10, wherein presenting the first most recent value according to the first arrangement further comprises presenting the different second most recent value of the second parameter of the different related parameters according to the second arrangement in response to a single stroke from a human user at an input for the particular display device.

12. The method as recited in claim 1, wherein the first arrangement of related parameters includes at least one of: a panel that displays vital signs; or a panel that displays fluids, electrolytes, nutrition (FEN) parameters; or a panel that displays respiratory parameters; or a panel that displays blood chemistry parameters; or a panel that displays cardiovascular system (CVS) parameters; or a panel that displays infectious disease (ID) parameters; or a panel that displays neurological parameters; or a panel that displays medications; or a panel that displays medication orders and laboratory orders and results for the last 24 hours.

13. The method as recited in claim 1, wherein the predetermined presentation style data further comprises a set of rules governing privacy requirements at the specified location for the subset of parameters.

14. A method for presenting patient data at the patient's bedside comprising:
sending, without human intervention to a particular display device located bedside for a particular patient, a plurality of most recent values from an electronic medical records (EMR) system, wherein the plurality of most recent values is associated in the EMR system with the particular patient for a corresponding plurality of parameters of a subset of fewer than all parameters available from the EMR system,
wherein the particular display device presents on an initial screen, according to a first arrangement and without human intervention, a first most recent value of the plurality of most recent values of related parameters in the subset;
wherein receiving the predetermined presentation style data further comprises receiving predetermined presentation style data that indicates a predetermined query message and a predetermined schedule; and
receiving the plurality of most recent values further comprises sending the predetermined query message to the EMR system on the predetermined schedule without human intervention and receiving at least one value of the plurality of most recent values in response to sending the predetermined query.

15. The method of claim 14, further comprising:
receiving without human intervention predetermined presentation style data that indicates the subset of fewer than all parameters available from the EMR system, and the first arrangement on the display device of the related parameters in the subset; and
sending without human intervention the predetermined presentation style data to the particular display device.

16. The method as recited in claim 14, wherein sending the plurality of most recent values without human intervention further comprises sending the plurality of most recent values on a predetermined schedule.

17. The method as recited in claim 14, wherein sending the plurality of most recent values without human intervention further comprises sending the plurality of most recent values in response to a query sent without human intervention from a client process on the particular display device.

18. The method as recited in claim 17, wherein the query from the client process is further received in response to a single stroke from a human user at an input for the particular display device.

19. The method as recited in claim 14, further comprising receiving initialization data that indicates a particular bedside where the particular display device is located.

20. The method as recited in claim 14, further comprising receiving initialization data that indicates the particular patient in a bed where the particular display device is located bedside.

21. The method as recited in claim 14, further comprising sending to the particular display device policy data that indicates an alteration to a value for a particular parameter in the subset before presentation at the particular display device.

22. The method as recited in claim 15, wherein the first arrangement includes a font size on the display device for a parameter of the subset, such that a value of the parameter is visible on the display device to multiple viewers more than five feet from the display device.

23. The method as recited in claim 15, wherein
receiving the predetermined presentation style data further comprises receiving predetermined presentation style data that indicates a different second arrangement on the display device of different related parameters in the subset; and
the particular display device presents the first most recent value according to the first arrangement for a first limited time and then presents a different second most recent value of a second parameter of the different related parameters according to the second arrangement for a second limited time.

24. The method as recited in claim 14, wherein the first arrangement of related parameters includes at least one of: a panel that displays vital signs; or a panel that displays fluids, electrolytes, nutrition (FEN) parameters; or a panel that displays respiratory parameters; or a panel that displays blood chemistry parameters; or a panel that displays cardiovascular system (CVS) parameters; or a panel that displays infectious disease (ID) parameters; or a panel that displays neurological parameters; or a panel that displays medications; or a panel that displays medication orders and laboratory orders and results for the last 24 hours.

25. A non-transitory computer-readable storage medium carrying one or more sequences of instructions for presenting patient data at a particular display device located bedside for a particular patient, wherein execution of the one or more sequences of instructions by one or more processors causes the one or more processors to perform the steps of:
receiving without human intervention predetermined presentation style data that indicates:
a subset of fewer than all parameters available from an electronic medical records (EMR) system;
a first arrangement on a display device of related parameters in the subset;
receiving without human intervention a plurality of most recent values from the EMR system, wherein the plurality of most recent values is associated in the EMR system with the particular patient for a corresponding plurality of parameters of the subset;
presenting, on an initial screen according to the first arrangement, a first most recent value of the plurality of most recent values;
wherein receiving the predetermined presentation style data further comprises receiving predetermined presentation style data that indicates a predetermined query message and a predetermined schedule; and
receiving the plurality of most recent values further comprises sending the predetermined query message to the EMR system on the predetermined schedule without human intervention and receiving at least one value of the plurality of most recent values in response to sending the predetermined query.

26. A non-transitory computer-readable storage medium carrying one or more sequences of instructions for presenting patient data at a particular display device located bedside for a particular patient, wherein execution of the one or more sequences of instructions by one or more processors causes the one or more processors to perform the step of:
sending, without human intervention to a particular display device located bedside for a particular patient, predetermined presentation style data that indicates:
a plurality of most recent values from an electronic medical records (EMR) system, wherein the plurality of most recent values is associated in the EMR system with the particular patient for a corresponding plurality of parameters of a subset of fewer than all parameters available from the EMR system,
wherein the particular display device presents on an initial screen, according to a first arrangement and without human intervention, a first most recent value of the plurality of most recent values of related parameters in the subset;
wherein sending the predetermined presentation style data further comprises receiving predetermined presentation style data that indicates a predetermined query message and a predetermined schedule; and
sending the plurality of most recent values further comprises receiving the predetermined query message from the particular display device on the predetermined schedule without human intervention and sending at least one value of the plurality of most recent values in response to receiving the predetermined query.

27. An apparatus for presenting patient data for a particular patient comprising:
a display for presenting data for viewing by a human user;
one or more processors;
logic encoded in one or more tangible media for
receiving predetermined presentation style data that indicates:
a subset of fewer than all parameters available from an electronic medical records (EMR) system;
a first arrangement on the display of related parameters in the subset;
receiving without human intervention a plurality of most recent values from the EMR system, wherein the plurality of most recent values is associated in the EMR system with the particular patient for a corresponding plurality of parameters of the subset;
presenting, on an initial screen according to the first arrangement, a first most recent value of the plurality of most recent values;
wherein receiving the predetermined presentation style data further comprises receiving predetermined presentation style data that indicates a predetermined query message and a predetermined schedule; and receiving the plurality of most recent values further comprises sending the predetermined query message to the EMR system on the predetermined schedule without human intervention and receiving at least one value of the plurality of most recent values in response to sending the predetermined query.

28. A system for presenting patient data for a particular patient:

a display device comprising:

a display for presenting data for viewing by a human user; and logic encoded in one or more tangible media for:

receiving predetermined presentation style data that indicates: a subset of fewer than all parameters available from an electronic medical records (EMR) system; a first arrangement on the display of related parameters in the subset;

receiving without human intervention a plurality of most recent values from the EMR system, wherein the plurality of most recent values is associated in the EMR system with the particular patient for a corresponding plurality of parameters of the subset;

presenting, on a default an initial screen according to the first arrangement, a first most recent value of the plurality of most recent values;

a server comprising logic encoded in one or more tangible media for sending, without human intervention, to the display device located bedside for the particular patient, the plurality of most recent values from the EMR system;

wherein receiving the predetermined presentation style data further comprises receiving predetermined presentation style data that indicates a predetermined query message and a predetermined schedule; and receiving the plurality of most recent values further comprises sending the predetermined query message to the EMR system on the predetermined schedule without human intervention and receiving at least one value of the plurality of most recent values in response to sending the predetermined query.

* * * * *